United States Patent
Jada

[11] Patent Number: 5,852,068
[45] Date of Patent: *Dec. 22, 1998

[54] HYDROPHILIC SILICONE DENTAL IMPRESSION COMPOSITION

[75] Inventor: Sivananda S. Jada, Cheshire, Conn.

[73] Assignee: Jeneric/Pentron Incorporated, Wallingford, Conn.

[*] Notice: This patent issued on a continued prosecution application filed under 37 CFR 1.53(d), and is subject to the twenty year patent term provisions of 35 U.S.C. 154(a)(2).

[21] Appl. No.: 766,595

[22] Filed: Dec. 12, 1996

[30] Foreign Application Priority Data

Mar. 11, 1993 [DE] Germany ............... 41 29 613

[51] Int. Cl.$^6$ ...................................... A61K 6/10
[52] U.S. Cl. ......................... 523/109; 525/477; 525/478
[58] Field of Search .................. 523/109; 525/477, 525/478

[56] References Cited

U.S. PATENT DOCUMENTS

| | | | |
|---|---|---|---|
| 4,222,983 | 9/1980 | August et al. | 524/862 |
| 4,616,076 | 10/1986 | Ona et al. | |
| 4,657,959 | 4/1987 | Bryan et al. | |
| 4,691,039 | 9/1987 | Aasen et al. | |
| 4,696,974 | 9/1987 | Sulc et al. | |
| 4,752,633 | 6/1988 | Aasen et al. | |
| 4,778,832 | 10/1988 | Futami et al. | |
| 4,877,854 | 10/1989 | Hattori et al. | |
| 5,086,148 | 2/1992 | Jochum et al. | |
| 5,145,915 | 9/1992 | Weitemeyer et al. | |
| 5,235,017 | 8/1993 | O'Lenick, Jr. | 528/26 |
| 5,260,401 | 11/1993 | O'Lenick, Jr. | 528/26 |
| 5,367,001 | 11/1994 | Itoh et al. | |

*Primary Examiner*—Melvyn I. Marquis
*Attorney, Agent, or Firm*—Fishman, Dionne, Cantor & Colburn

[57] ABSTRACT

A dental impression composition for use in the preparation of the oral tissue models comprising a dimethicone-based polysiloxane polyester polymer having terminal fluorinated alkoxy substituents such that the fluorine content of the polysiloxane polyester is in the range from about 5% to about 30% by weight, and having the general formula A—[—B—C—]$_x$—A, wherein x is an integer greater than 1; A is a fluorinated alkoxy group having the formula $F_3C(CF_2)_n(CH_2)_mO$— wherein n is an integer from 3 to 17 and m is an integer from 2 to 4; B is a diacid; and C is a dimethicone-based polysiloxane copolyol having the formula:

$$Me_3Si\text{—}[\text{—}OSiMeR^1\text{—}]\text{—}[\text{—}OSiMeR^1\text{—}]_o\text{—}[\text{—}OSiMeR\text{—}]_q\text{—}OSiMe_3$$

wherein Me is methyl, R is methyl or phenyl, o is an integer in the range from 1 to 19, q is an integer in the range from 0 to 200, and R$^1$ is a polyoxyalkylene substituent having the formula $$\text{—}(\text{—}CH_2)_3\text{—}(DO)_a(EO)_b(FO\text{—})_c\text{—}$$

wherein the propyl groups is linked to the silicon atom and DO, EO, and FO are the same or different, being linear or branched oxyalkylene groups having from 2 to 6 carbons, a and b are each independently integers in the range from 1 to 19, and c is an integer from 1 to 20. Preferably, DO is $CH_2CH_2O$, EO is $CH_2CH(CH_3)O$, and FO is $CH_2CH_2O$. Use of the foregoing polysiloxane polyester polymer results in a dental impression material with optimal hydrophilicity, increased tear strength, and improved water adsorption.

10 Claims, No Drawings

HYDROPHILIC SILICONE DENTAL IMPRESSION COMPOSITION

BACKGROUND OF INVENTION

1. Field of the Invention

The present invention relates to a dental impression composition for use in the preparation of the oral tissue models required for the preparation of dental prostheses such as crowns, inlays or dentures. In particular, the invention relates to a composition comprising a dimethicone-based polysiloxane polyester polymer having terminal fluorinated alkoxy substituents, which results in a dental impression material with optimal hydrophilicity, increased tear strength and improved water adsorption.

2. Relevant Art

Dental impression materials are used to accurately form an impression of the shape, size, and relative locations of both hard and soft tissues within the mouth. Typically, a gypsum slurry is then used to form a model from the impression. Elastically deformable impression materials are used so that upon removal of the impression from within the mouth, their deformation, if any, is restored to the original form. However, it is equally important that the material resist farther deformation or shrinkage, in order to provide an accurate model. Commonly used impression materials include agar, alginates, polysulfide rubbers, polyether rubbers, silicone rubbers, and the like.

While factors such as taste, odor, toxicity, viscosity, cure speed, ease of demolding and strength after cure are all important, accuracy of the formed impression is the most important. Agar or alginate impression materials show a suitable degree of elasticity from the clinical point of view, are easy to handle, and relatively inexpensive. However, they have low tear strength, may permanently deform upon removal from the mouth, and tend to deform further over time due to their high moisture content. For these reasons, synthetic rubber-based impression materials are preferred, as they show a suitable degree of elasticity, are easy to handle, have a high tear strength, give rise to fairly small permanent deformation upon removal from the mouth, and provide cured products which show only limited dimensional changes with the lapse of time.

Polysulfide rubbers are disadvantageous in that they have a strong, offensive odor, and cure too slowly. Polyether rubbers have reduced elasticity, bad taste, foul smell, are very sticky, and are greatly affected by moisture. Room-temperature vulcanization (RTV) silicone rubbers have therefore become the impression material of choice, as they are essentially tasteless and odorless, cure quickly, and have both excellent elasticity and dimensional stability.

RTV silicone rubber is classified as either condensation or addition type. Each is generally formed from a two component curable silicone prepolymer system, comprising a silicone polymer base with a crosslinking agent and a metal and/or peroxide catalyst. Condensation type silicone rubbers are formed from a curable silicone prepolymer comprising a first silicone polymer base component, generally consisting of a hydroxy dimethyl polysiloxane having terminal or pendant hydroxyl groups, and a second component comprising a crosslinking agent generally consisting of a silicic acid ester, for example an alkyl orthosilicate such as tetraethyl orthosilicate, and an organic tin catalyst. RTV addition-curing silicone rubbers, on the other hand, are formed from a curable silicone prepolymer comprising a silicone polymer base component generally consisting of a hydrogen polymethylsiloxane having at least one terminal or pendant hydrogen, and a second component comprising a vinyl polymethylsiloxane crosslinking agent and a platinum catalyst.

One drawback to the use of silicone rubbers as dental impression materials has been their hydrophobicity, making it difficult to take precise impressions of the details of the tooth and/or hard tissue when it is wetted with blood, saliva, or other fluids. When making the impression, the blood, saliva, or other fluids are forced into the margins of the teeth or pits and fissures in the teeth by the hydrophobic silicone impression material, rendering it difficult to take detailed and precise impressions because of the high surface tension of the silicone materials. The dentist or operator may attempt to dry the oral cavity by blowing air into the oral cavity, but this is cumbersome not only for the operator but also the patient, particularly where the patient is bleeding. The hydrophobicity of silicone dental impression materials also prevents the formation of accurate models formed from gypsum slurries.

Repeated attempts have been made to render silicone dental impression materials more hydrophilic by including various ionic or non-ionic surfactants in the composition, as is described for example in DE 4129613 to Hefner et al., U.S. Pat. No. 4,657,959 to Bryan et al., U.S. Pat. No. 4,691,039 to Aasen et al., and U.S. Pat. No. 4,752,633 to Aasen et al. U.S. Pat. No. 4,778,832 to Futami discloses use of a protein additive such as albumin as well as a silicone oil or non-ionic surfactant to increase hydrophilicity. However, these additives suffer from certain drawbacks, including instability in moist air, deactivation of platinum catalyst complexes, and reduction in the tear strength of the dental impression. They may swell first in water, and then dissolve gradually, and undergo phase separation in the vinyl-terminated polydimethylsiloxane base components. Thus, there remains a need for silicone dental impression materials that are more hydrophilic, with improved tear strength and minimal permanent deformation.

SUMMARY OF INVENTION

The above-discussed and other drawbacks and deficiencies of the prior art are overcome or alleviated by the dental impression composition of the present invention, comprising a curable silicone prepolymer and a dimethicone-based polysiloxane polyester polymer having terminal fluorinated alkoxy substituents sufficient to increase the hydrophilicity of the cured silicone polymer so that said composition, when cured, has a three minute water contact angle at or below about 73°. Such concentration is generally in the range from about 0.5 percent to about 75 percent by weight of the curable silicone prepolymer. The cured composition thus obtained is readily wet by water, yet retains the other desirable properties characteristic of silicones. The composition facilitates the making of more accurate dental impressions and the production of more accurate models.

The polysiloxane polyester polymer has the general formula:

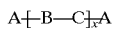

wherein x is an integer greater than 1, and such that the fluorine content of the polysiloxane polyester is in the range from about 5% to about 30% by weight; wherein A is a fluorinated alkoxy group having the formula

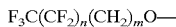

wherein n is an integer from 3 to 7 and y is an integer from 2 to 4; and further wherein B is dimer acid or other diacid, for example, adipic acid, succinic acid, maleic acid, or dodecanedioic acid; and still further wherein C is a dimethicone-based polysiloxane copolyol having the following formula:

$$Me_3Si{+}OSiMeR^1{\}{+}{[}OSiMeR^1{]}_o{+}{[}OSiMeR{]}_q{-}OSiMe_3$$

wherein Me is methyl, R is methyl or phenyl, o is an integer in the range from 1 to 19, q is an integer in the range from 0 to 200, and $R^1$ is a hydroxylated polyoxyalkylene substituent having the formula $$-(-CH_2)_3O(DO)_a(EO)_b(FO)_c-$$

wherein the propyl group is linked to the silicone atom and DO, EO, and FO are the same or different, being linear or branched oxyalkylene groups having from 2 to 6 carbons, a and b are each independently integers in the range from 0 to 20, and c is an integer in the range from 1 to 20. Preferably, DO is $CH_2CH_2O$, EO is $CH_2CH(CH_3)O$, and FO is $CH_2CH_2O$. Importantly, the polysiloxane polymer is end-capped as shown by trimethyl silyl groups.

Preferably, the curable silicone dental impression prepolymer composition in accordance with the present invention comprises:

(A) a polyorganohydrogensiloxane having at least one silicon-bonded hydrogen atom;

(B) a silicone polymer having at least two alkenyl groups;

(C) the above-described dimethicone-based polysiloxane polyester polymer;

(D) a platinum catalyst; and (E) inorganic filler.

In another embodiment, the present invention comprises a molded hydrophilic silicone article prepared by shaping and curing the above-described composition. Such articles include dental impressions, lithographic plates, release liners, reflective sheeting, adhesives, coatings and sealants.

In yet a further embodiment, the present invention provides a method for making a dental impression, comprising the step of making a negative model of teeth and/or hard tissue using the above-described compositions.

DETAILED DESCRIPTION OF THE INVENTION

In the practice of the present invention, the curable silicone prepolymer composition can be a one-part or multiple-part composition cured by the presence of adventitious moisture, crosslinking agents, catalysts, and/or heat. Most preferred are two-part addition cure or condensation cure compositions of the RTV variety. The composition contains a "curable silicone prepolymer", that is, a polysiloxane having one or more functional groups which enable the prepolymer to be polymerized or cured to a higher molecular weight. Suitable silicone prepolymers are well-known in the art and are described, for example, in "Silicones", *Kirk-Othmer Encyclopedia of Chemical Technology*, 3rd Ed., 20, 922–962 (1982), the disclosure of which is incorporated herein by reference.

Two-part RTV silicone addition cure compositions are especially preferred. As discussed above, such compositions are well-known in the art, and generally comprise a vinyl polymethylsiloxane, a hydrogen polymethylsiloxane crosslinking agent and a platinum-based catalyst.

Preferably, the vinyl-terminated polydimethylsiloxanes conform to the following structure:

$$H_2C{=}CHSi(CH_3)_2{-}{[}{-}Si(CH_3)_2{-}O{-}{]}_e{-}{[}SiCH_3RO{-}{]}_g{-}Si(CH_3)_2CH{=}CH_2$$

wherein R is alkyl or allyl, e is about 75 or higher, and g is about 12 or higher. Such vinyl-terminated polydimethylsiloxanes are commercially available.

Preferred silicone crosslinkers include the tetrafunctional silane $Si(OSiMe_2H)_4$, a pentafunctional cyclic siloxane $(OSiMe_2H)_5$, and a hydridofunctional homopolymer $Me_3Si(OSiMeH)_{37}OSiMe_3$, which has a nominal functionality of 37.

The dental impression composition according to the present invention further comprises a polysiloxane polyester polymer having the general formula:

$$A{+}B{-}C{]}_xA$$

wherein x is an integer greater than 1, and such that the fluorine content of the polysiloxane polyester is in the range from about 5% to about 30% by weight;

wherein A is a fluorinated alkoxy group having the formula $$F_3C(CF_2)_n(CH_2)_mO{-}$$

wherein n is an integer from 3 to 17 and m is an integer from 2 to 4;

wherein B is dimer acid or other diacid, for example, adipic acid, succinic acid, maleic acid, or dodecanedioic acid; and wherein C is a dimethicone-based polysiloxane copolyol having the following formula:

$$Me_3Si{+}OSiMeR^1{\}{+}{-}OSiMeR^1{]}_o{+}{-}OSiMeR{]}_q{-}OSiMe_3$$

wherein Me is methyl, R is methyl or phenyl, o is an integer in the range from 1 to 19, q is an integer in the range from 0 to 200, and $R^1$ is a hydroxylated polyoxyalkylene substituent having the formula $$-({-}CH_2)_3O(DO)_a(EO)_b(FO{-})_c{-}$$

wherein the propyl group is linked to the silicone atom and DO, EO, and FO are the same or different, being linear or branched oxyalkylene groups having from 2 to 6 carbons, a and b are each independently integers in the range from 0 to 20, and c is an integer from 1 to 20. Preferably, DO is $CH_2CH_2O$, EO is $CH_2CH(CH_3)O$, and FO is $CH_2CH_2O$.

Importantly, the copolyol portion of the polysiloxane polymer is dimethicone-based, that is, end-capped by trimethyl silyl groups as shown. Such polyester polysiloxanes are generally prepared from the esterification of dimer acid or other diacid with the appropriate dimethicone-based polysiloxane polyol and fluorinated alcohol. As the fluorinated alcohol has only one hydroxyl group, it will be chain-terminating. Preferred polyester polysiloxanes are described in U.S. Pat. No. 5,235,017 to O'Lenick, Jr., which is incorporated herein by reference in its entirety. One particularly preferred polyester polysiloxane polymer is available commercially from Siltech, Inc., under the trade name SILWAX WD-F, wherein B is dimer acid, R is methyl, n is 10, m is 2, o is 4, q is 29, D is ethyl, F is ethyl, a is 6, b is zero, and c is 1. Dimer acid is known in the art and prepared by the thermal condensation of unsaturated fatty acids catalyzed by a small amount of montmorillonite clay to yield cyclic or acyclic diacids. Dimer acid is described in U.S. Pat. No. 5,235,017 to O'Lenick at columns 3 and 4.

The polysiloxane polyester polymer is present in the composition in an amount effective to impart hydrophilicity to the cured polymer, so that the composition, when cured, has a three minute water contact angle at or below about 73°. The preferred amount of surfactant will depend upon the particular curable silicone prepolymer used, the polysiloxane polymer, and the amounts and types of other adjuvants present in the composition. Generally, the polysiloxane polymer is present in the range from about 0.5 percent to about 75 percent by weight of the curable silicone prepolymer.

A single polysiloxane polyester polymer may be used, or in combination with other polysiloxane polyester polymers.

The dental impression compositions of the present invention may additionally comprise inorganic fillers, including but not limited to those known in the art such as diatomacious earth, calcium carbonate, silicic acid, calcium sulfate, zirconium silicate, zirconium oxide, titanium oxide, and zinc oxide. Surface-treated fillers may also be used, such surface treatments including silanization and the like.

Other additives which may be used in the present invention include polymerization inhibitors, colorants, perfumes, fluidity regulators, reinforcing agents, plasitcizers, and the like.

Typically, the compositions according to the present invention are packaged, stored, and used in the conventional manner for curable silicone prepolymer systems. Thus, the two components are generally stored separately, the first component comprising the silicone polymer base component, fillers and other adjuvants; and the second component comprising the cross-linking agent and catalyst. The polysiloxane polymer may be present in either component, or both. However, where the polysiloxane polymer may react with constituents of either component, then it should be added only to the non-reactive component.

The present invention is further illustrated by the following non-limiting examples.

General Procedures

Dental impression compositions were prepared by mixing the base polymer components and catalyst polymer components (parts by weight) described below in a kneader. In all examples, the polysiloxane polyester polymer is SILWAX WD-F from Siltech, Inc., wherein B is dimer acid, R is methyl, n is 10, m is 2, o is 4, q is 29, D is ethyl, F is a is ethyl, 6, b is zero, and c is 1.

The dynamic contact angle, θ, is measured by the tangent at the three phase solid/liquid/vapor phase interface using the dynamic contact angle analysis system DCA-315 from Cahn Instruments, Cerritos, Calif. As the probe solid surface is held in a fixed position by the Cahn Electrobalance, distilled water contained in a beaker is programmed to move at a constant rate to scan the surface of the solid and produce a unique contact angle hysteresis curve. By applying the principles of the well-established Wilhelmy technique, the dynamic contact angle is calculated from the modified Young equation as follows:

$$\cos \theta = F/s.t.*P$$

where

F is the wetting force recorded by the balance;

s.t. is the surface tension of the distilled water; and

P is the wetted perimeter (or circumference) of the solid.

EXAMPLE 1

The base polymer was prepared by mixing 77 parts of polydimethylsiloxane containing terminal vinyl groups and with a mixture of fluids having the viscosity of 1,000,000 or over, 65,000 and 1,000 mPa.s at 20° C., 6.5 parts of polydimethylsiloxane containing hydridosilyl groups, 1 part polyester polysiloxane polymer according to the present invention, and enough parts silanized inorganic filler and colored inorganic pigments to make a total of 100 parts in a kneader.

The catalyst polymer was prepared by mixing 67.5 parts of polydimethylsiloxane containing terminal vinyl groups and with a mixture of fluids having the viscosity of 1,000,000 or over, 65,000 and 1,000 mPa.s at 20° C.,0.4 parts of catalyst made from a mixture of 1,3-divinyltetramethyl disiloxane and chloroplatinic acid, 0.1 parts of polymerization inhibitor and enough parts inorganic filler to make a total of 100 parts in a kneader.

The measured receding contact angle was 73.0.

EXAMPLE 2

The base polymer was prepared by mixing 77 parts of polydimethylsiloxane containing terminal vinyl groups and with a mixture of fluids having the viscosity of 1,000,000 or over, 65,000 and 1,000 mPa.s at 20° C.,6.5 parts of polydimethylsiloxane containing hydridosilyl groups, 10 parts of polyester polysiloxane polymer and enough parts silanized inorganic filler and colored inorganic pigments to make a total of 100 parts in a kneader.

The catalyst polymer was prepared by mixing 67.5 parts of polydimethylsiloxane containing terminal vinyl groups and with a mixture of fluids having the viscosity of 1,000,000 or over, 65,000 and 1,000 mPa.s at 20 ° C.,0.4 parts of catalyst made from a mixture of 1,3-divinyltetramethyl disiloxane and chloroplatinic acid, 0.1 parts of polymerization inhibitor and enough parts inorganic filler to make a total of 100 parts in a kneader.

The measured average receding contact angle was 70.7.

EXAMPLE 3

The base polymer was prepared by mixing 77 parts of polydimethylsiloxane containing terminal vinyl groups and with a mixture of fluids having the viscosity of 1,000,000 or over, 65,000 and 1,000 mPa.s at 20 C., 6.5 parts polydimethylsiloxane containing hydridosilyl groups, 30 parts of polyester polysiloxane polymer and enough parts silanized inorganic filler and colored inorganic pigments to make 100 parts in a kneader.

The catalyst polymer was prepared by mixing 67.5 parts of polydimethylsiloxane containing terminal vinyl groups and with a mixture of fluids having the viscosity of 1,000,000 or over, 65,000 and 1,000 mPa.s at 20° C.,0.4 parts of catalyst made from a mixture of 1,3-divinyltetramethyl disiloxane and chloroplatinic acid, 0.1 parts of polymerization inhibitor and enough parts inorganic filler to make 100 parts in a kneader.

The measured receding contact angle was 67.4.

EXAMPLE 4

The base polymer was prepared by mixing 77 parts of polydimethylsiloxane containing terminal vinyl groups and with a mixture of fluids having the viscosity of 1,000,000 or over, 65,000 and 1,000 mPa.s at 20° C., 6.5 parts of polydimethylsiloxane containing hydridosilyl groups, 60 parts of polyester polysiloxane polymer and the rest constituted silanized inorganic filler and colored inorganic pigments in a kneader to make a total of 100 parts.

The catalyst polymer was prepared by mixing 67.5 parts of polydimethylsiloxane containing terminal vinyl groups and with a mixture of fluids having the viscosity 1,000,000 or over, 65,000 and 1,000 mPa.s at 20° C., 0.4 parts of catalyst made from a mixture of 1,3-divinyltetramethyl disiloxane and chloroplatinic acid, 0.1 parts of polymerization inhibitor and enough parts inorganic filler in a kneader to make a total of 100 parts.

The measured average receding contact angle was 67.4.

EXAMPLE 5

The base polymer was prepared by mixing 77 parts of polydimethylsiloxane containing terminal vinyl groups and with a mixture of fluids having the viscosity of 1,000,000 or over, 65,000 and 1,000 mPa.s at 20° C., 6.5 parts of polydimethylsiloxane containing hydridosilyl groups, 75 parts of polyester polysiloxane polymer and the rest constituted silanized inorganic filler and colored inorganic pigments in a kneader to make 100 parts total.

The catalyst polymer was prepared by mixing 67.5 parts of polydimethylsiloxane containing terminal vinyl groups and with a mixture of fluids having the viscosity of 1,000,000 or over, 65,000 and 1,000 mPa.s at 20° C., 0.4 parts of catalyst made from a mixture of 1,3-divinyltetramethyl disiloxane and chloroplatinic acid, 0.1 parts of polymerization inhibitor and enough parts inorganic filler in a kneader to make 100 parts total.

The measured receding contact angle is 67.3.

In the above examples, the dental impression compositions of the present invention show improved wettability, improved tear strength, and improved water absorption. Additionally, they are odorless and tasteless, easy to mix, have excellent deformation properties, and do not shrink with time.

While preferred embodiments have been shown and described, various modifications and substitutions may be made thereto without departing form the spirit and scope of the invention. Accordingly, it is to be understood that the present invention has been described by way of illustration and not limitation.

What is claimed is:

1. A curable composition comprising a mixture of
   (a) curable silicone prepolymer; and
   (b) a polyester polysiloxane polymer having the formula:

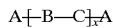

wherein x is an integer greater than 1, and such that the fluorine content of the polysiloxane polyester is in the range from about 5% to about 30% by weight;
   wherein A is a fluorinated alkoxy group having the formula

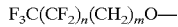

wherein n is an integer from 3 to 17 and m is an integer from 2 to 4;
   wherein B is a diacid; and
   wherein C is a dimethicone-based polysiloxane copolyol having the following formula:

wherein Me is methyl, R is methyl or phenyl, o is an integer in the range from to 19, q is an integer in the range from 0 to 200, and $R^1$ is an oxyalkylene substituent having the formula

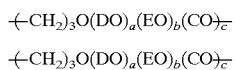

wherein the propyl group is linked to the silicone atom and, DO, EO and FO are the same or different, being linear or branched polyoxyalkylene groups having from 2 to 6 carbons, a and b are each independently integers in the range from 0 to 20, and c is an integer in the range from 1 to 20;
   and further wherein said polyester polysiloxane polymer is present in a sufficient amount to impart a three minute water contact angle at or below about 73° upon cure of the mixture.

2. The composition of claim 1, wherein the curable silicone prepolymer comprises
   a two-part room temperature vulcanization addition cure or condensation cure polysiloxane.

3. The composition of claim 1, wherein the curable silicone prepolymer comprises
   (a) a polyorganohydrogensiloxane having at least one silicon-bonded hydrogen atom; and wherein the composition further comprises
   (b) a silicone polymer having at least two alkenyl groups;
   (c) a platinum catalyst; and
   (d) inorganic filler.

4. The composition of claim 1, wherein
   B is dimer acid, R is methyl, n is 10, m is 1, o is 4, q is 29, D is ethyl, F is ethyl, a is 6, b is zero, and c is 1.

5. The composition of claim 1, wherein
   the curable silicone prepolymer is a two-part room temperature vulcanization addition cure polysiloxane composition; and
   B is dimer acid, R is methyl, n is 10, m is 2, o is 4, q is 29, D is ethyl F is ethyl, a is 6, b is zero, and c is 1.

6. The composition of claim 1, wherein the composition is in the form of a cured composition having the polyester polysiloxane polymer dispersed therein, the cured composition comprising a dental impression, the impression comprising a negative mold of an oral tissue.

7. A method for making a dental impression, comprising
   (a) providing a curable silicone prepolymer; and
   a polyester polysiloxane polymer having the formula:

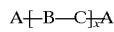

wherein x is an integer greater than 1, and such that the fluorine content of the polysiloxane polyester is in the range from about 5% to about 30% by weight;
   wherein A is a fluorinated alkoxy group having the formula

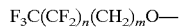

wherein n is an integer from 3 to 17 and m is an integer from 2 to 4;
   wherein B is a diacid; and
   wherein C is a dimethicone-based polysiloxane copolyol having the following formula:

wherein Me is methyl, R is methyl or phenyl, o is an integer in the range from 2 to 20, q is an integer in the range from 0 to 200 and $R^1$ is an oxyalkylene substituent having the formula

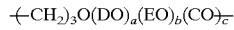

wherein the propyl group is linked to the silicone atom and DO, EO, and FO are the same or different, being linear or branched polyoxyalkylene groups having from 2 to 6 carbons, a and b are each independently integers in the range from 0 to 20 and c is an integer in the range from 1 to 19; the polyester polysiloxane polymer being present in a sufficient amount to impart a three minute water contact angle at or below about 73° upon cure of the mixture; and (b) curing the composition to make a negative mold of oral tissue.

8. The method of claim 7, wherein the curable silicone prepolymer composition comprises (a) a polyorganohydrogensiloxane having at least one silicon-bonded hydrogen atom; and wherein the composition further comprises (b) a silicone polymer having at least two alkenyl groups;

(c) a platinum catalyst; and (d) inorganic filler.

9. The method of claim 7, wherein B is dimer acid, R is methyl, n is 10, m is 1, o is 4, q is 29, D is ethyl, F is ethyl, a is 6, b is zero, and c is 1.

10. The method of claim 7, wherein the curable silicone prepolymer is a two-part room temperature vulcanization addition cure polysiloxane composition; and B is dimer acid, R is methyl, n is 10, m is 2, o is 4, q is 29, D is ethyl, F is ethyl, a is 6, b is zero, and c is 1.

* * * * *

UNITED STATES PATENT AND TRADEMARK OFFICE
CERTIFICATE OF CORRECTION

PATENT NO.    : 5,852,068
DATED         : December 22, 1998
INVENTOR(S)   : Sivananda S. Jada It is certified that error appears in the above-identified patent and that said Letters Patent is hereby corrected as shown below:

Column 3,
Line 18, delete "20" (second occurence) and insert therefor -- 19 --.

Column 4,
Line 1, delete "]c" and insert therefor -- ]e -- in the formula.
Line 35, delete "hydrozylated".
Line 44, delete "20" (second occurrence) and insert therefor -- 19 --.

Column 5,
Line 41, after "F is", insert -- ethyl, --.
Line 42, delete "ethyl,".

Column 7,
Line 62, insert -- 1 -- between "from" and "to".

Column 8,
Line 5, delete "20" (second occurrence) and insert therefor -- 19 --.
Line 32, insert coma -- , -- between "ethyl" and "F".

Signed and Sealed this

Eleventh Day of March, 2003

JAMES E. ROGAN
*Director of the United States Patent and Trademark Office*